US012161744B2

(12) United States Patent
Gopaul et al.

(10) Patent No.: US 12,161,744 B2
(45) Date of Patent: Dec. 10, 2024

(54) *Cordyceps* CONTAINING TOPICAL SKIN CARE FORMULATION

(71) Applicant: NSE Products, Inc., Provo, UT (US)

(72) Inventors: Remona Gopaul, Lehi, UT (US); Jin Namkoong, Provo, UT (US); Aaron Ballantyne, Pleasant Grove, UT (US); Helen Knaggs, Orem, UT (US); Deanna Carter, Orem, UT (US); Dale Kern, Hyde Park, UT (US)

(73) Assignee: NSE PRODUCTS, INC., Provo, UT (US)

( * ) Notice: Subject to any disclaimer, the term of this patent is extended or adjusted under 35 U.S.C. 154(b) by 330 days.

(21) Appl. No.: 15/174,972

(22) Filed: Jun. 6, 2016

(65) Prior Publication Data
US 2017/0020805 A1 Jan. 26, 2017

Related U.S. Application Data

(60) Provisional application No. 62/171,934, filed on Jun. 5, 2015.

(51) Int. Cl.
*A61K 36/068* (2006.01)
*A61K 8/19* (2006.01)
*A61K 8/34* (2006.01)
*A61K 8/60* (2006.01)
*A61K 8/81* (2006.01)
*A61K 8/9728* (2017.01)
*A61K 36/00* (2006.01)
*A61Q 19/00* (2006.01)
*A61Q 19/08* (2006.01)

(52) U.S. Cl.
CPC .............. *A61K 8/606* (2013.01); *A61K 8/19* (2013.01); *A61K 8/345* (2013.01); *A61K 8/8147* (2013.01); *A61K 8/8152* (2013.01); *A61K 8/9728* (2017.08); *A61K 36/068* (2013.01); *A61Q 19/00* (2013.01); *A61Q 19/007* (2013.01); *A61Q 19/08* (2013.01); *A61K 2236/00* (2013.01); *A61K 2800/48* (2013.01)

(58) Field of Classification Search
CPC .................................................. A61K 36/068
See application file for complete search history.

(56) References Cited

U.S. PATENT DOCUMENTS

| 7,718,416 B1 | 5/2010 | Zhu | |
| 2006/0018860 A1* | 1/2006 | Chen | A61K 31/7048 424/70.14 |
| 2009/0028895 A1* | 1/2009 | Smith | A61K 31/045 424/195.15 |
| 2013/0195911 A1* | 8/2013 | Baier | A61K 9/0014 424/195.15 |

FOREIGN PATENT DOCUMENTS

| CA | 2347979 C | * | 1/2009 | ............. A61K 31/70 |
| CN | 100488521 C | * | 5/2009 | ............. A61K 36/08 |
| CN | 103989617 A |  | 8/2014 | |
| KR | 1020140042964 |  | 4/2014 | |

OTHER PUBLICATIONS drug.com; "Baeknyondongan Chi"; https://web.archive.org/web/20130328204107/www.drugs.com/otc/116014/baeknyondongan-chi.html ; Accessed on Oct. 13, 2016; 4 Pages.
cosmetic-ingredients.net; "Estee Lauder";http://web.archive.org/web/20150321051938/http://cosmetic-ingredients.net/product.php?type=Eye%20Treatment&brand=41 ; Accessed on Oct. 13, 2016; 5 Pages.
Wu et al.; "Effect of Cordceps Sinensis on the Expression of ICAM-1 and VCAM-1 in the Kidney of Spontaneously Hypertensive Rats"; Journal of Central South University-Medical Sciences; (2010); pp. 152-158; vol. 35, Issue 2.
International search report issued (Oct. 19, 2016); for PCT Application No. PCT/US2016/036094; filed (Jun. 6, 2016); 22 pages.

* cited by examiner

*Primary Examiner* — Aaron J Kosar
*Assistant Examiner* — Randall O Winston
(74) *Attorney, Agent, or Firm* — Thorpe North & Western, LLP; David W. Osborne

(57) ABSTRACT

The present disclosure relates to extracts of *Cordyceps* spp., topical formulations containing extracts of *Cordyceps* spp., methods of formulating the extract and formulations, and methods of use. In one embodiment the *Cordyceps* spp. is *Cordyceps sinensis*.

15 Claims, 2 Drawing Sheets

*Cordyceps* CONTAINING TOPICAL SKIN CARE FORMULATION

PRIORITY DATA

This application claims the benefit of U.S. Provisional Patent Application Ser. No. 62/171,934, filed on Jun. 5, 2015, which is incorporated herein by reference.

BACKGROUND

The cosmetic industry covers a wide variety of products which can include naturally or synthetically derived compounds for application to the skin. Skin care compositions can be topically applied for: cleansing, moisturizing, deodorizing, enhancing or altering a person's appearance, etc. Cosmetics come in a variety of forms including, but not limited to: creams, lotions, powders, oils, gels, and butters, to name a few.

One particular area of focus in the cosmetics industry are products geared towards reducing the signs of aging. The anti-aging market is concerned with reduction or elimination of wrinkles, fine lines, age spots, hyper pigmentation, dry skin, uneven skin tone, texture, pore size, and overall radiance. Consumers are increasingly demanding natural products and product developers are ever challenged to find formulations that contain active natural ingredients that can improve more than one sign of aging, while remaining economically feasible. As such formulations that include naturally derived cosmetic compounds continue to be sought.

BRIEF DESCRIPTION OF THE FIGURES

Features and advantages of the invention will be apparent from the detailed description that follows, which taken in conjunction with the accompanying figures, together illustrate the features of the invention. It is understood that these drawings merely depict exemplary results and are not, therefore, to be considered limiting in scope. Furthermore, it will be readily appreciated that the results, as generally described and illustrated in the figures herein, are averages based on clinical studies and that individual results will vary based on an individual's skin type and genetic profile.

DETAILED DESCRIPTION

Figure 1:
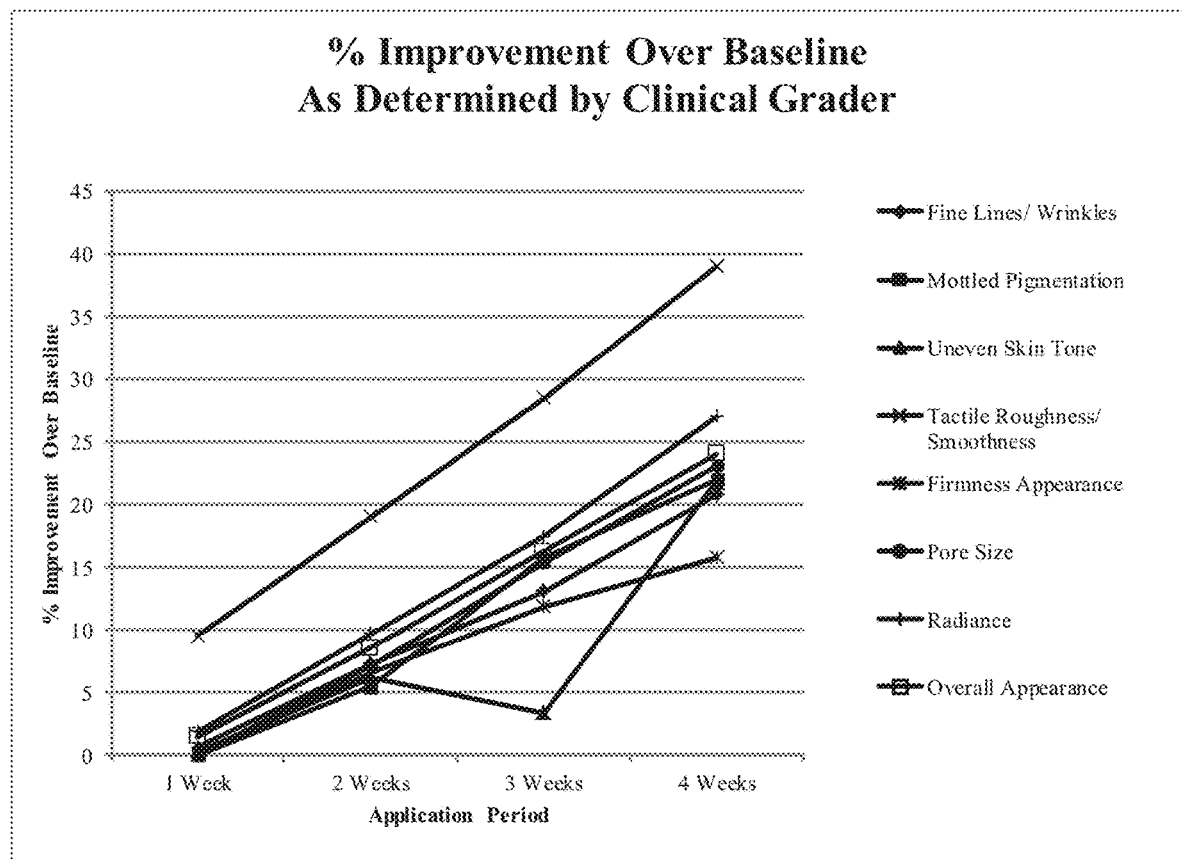
FIG. 1 shows the clinical grader's results for percent improvement over baseline of a variety of treated dermatological conditions following the application of a topical formulation that includes a *Cordyceps* extract.

Reference will now be made to exemplary invention embodiments and specific language will be used herein to describe the same. It will nevertheless be understood that no limitation in scope is thereby intended. Alterations and further modifications of inventive features described herein, and additional applications of inventive principles which would occur to one skilled in the relevant art having possession of this disclosure, are to be considered as inventive subject matter. Further, before particular embodiments are disclosed and described, it is to be understood that this disclosure is not limited to the particular processes and materials disclosed herein as such may vary to some degree.

It is also to be understood that the terminology used herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "an enhancer" includes one or more of such enhancers.

In this disclosure, "comprises," "comprising," "comprised," "containing" and "having" and the like can have the meaning ascribed to them in U.S. patent law and can mean "includes," "including," and the like, and are generally interpreted to be open ended terms. The term "consisting of" is a closed term, and includes only the methods, compositions, components, systems, steps, or the like specifically listed, and that which is in accordance with U.S. patent law. "Consisting essentially of" or "consists essentially" or the like, when applied to devices, methods, compositions, components, structures, steps, or the like encompassed by the present disclosure, refer to elements like those disclosed herein, but which may contain additional structural groups, composition components, method steps, etc. Such additional devices, methods, compositions, components, structures, steps, or the like, etc., however, do not materially affect the basic and novel characteristic(s) of the devices, compositions, methods, etc., compared to those of the corresponding devices, compositions, methods, etc., disclosed herein. In further detail, "consisting essentially of" or "consists essentially" or the like, when applied to the methods, compositions, components, systems, steps, or the like encompassed by the present disclosure have the meaning ascribed in U.S. patent law and is open-ended, allowing for the presence of more than that which is recited so long as basic or novel characteristics of that which is recited is not changed by the presence of more than that which is recited, but excludes prior art embodiments. In this specification when using an open ended term, like "comprising" or "including," it is understood that direct support should be afforded also to "consisting essentially of" language as well as "consisting of" language as if stated explicitly and vice versa.

As used herein, "active constituent" refers to a molecule, compound, mixture, or ingredient that has a measurable physiologic effect on a subject when administered thereto in an appreciable amount, such as an effective, or therapeutically effective amount. Like terms such as "active fraction," "active component," and "active agent" can be used interchangeable therewith.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 mg to 2.0 mg" should be interpreted to include not only the explicitly recited values of about 0.01 mg to about 2.0 mg, but also include individual values and sub-ranges within the indicated range. Thus, included in this numerical range are individual values such as 0.5 mg, 0.7 mg, and 1.5 mg, and sub-ranges such as from 0.5 mg to 1.7 mg, from 0.7 mg to 1.5 mg, and from 1.0 mg to 1.5 mg, etc. This same principle applies to ranges reciting only one numerical value. Furthermore, such an interpretation should apply regardless of the breadth of the range or the characteristics being described.

As used herein, "aging" and "senescence" may be used interchangeably to refer to the accumulation of changes that occur in a living organism over time. Such changes can range from those affecting genetic and cellular function to those affecting the function of organs, organ systems, or the whole organism. Senescence in particular refers to such changes occurring after an organism has attained biological maturity and which may progress until the eventual death of the organism. The term "effects of aging" as used herein particularly to refers to age-related changes in genetic function, such as changes in transcription of individual genes as well as transcriptional profiles of groups of genes.

As used herein, "age-related dermatological symptoms or conditions" and the like refers to visible symptoms on the surface of skin that occur as a consequence of aging. These symptoms include, but are not limited to include: wrinkles, fine lines, mottled pigmentation, uneven skin tone, tactile roughness/smoothness (i.e. texture), firmness in appearance, overall skin firmness, firmness around eyes, hydration, skin smoothness, skin tone, skin brightness, noticeably of pores, skin spots, skin softness, or the like.

As used herein "*Cordyceps* fungus," "*Cordyceps* spp." or "*Cordyceps*" refers to a division of ascomycete fungus whose species, are typically entomopathogenic. Exemplary species include without limitation *O. sinensis, C. sinensis, C. militaris, C. ophioglossoides, C. capita, C. pseudomilitaris, C. cardinalis, paecilomyces hepiali*, (*P. hepiali*), and *hirsutella sinensis* (*H sinensis*). Combinations of species, anamorphs, strains, and hybrids thereof are also encompassed by such terms. In one embodiment, *cordyceps* or *cordyceps* fungus can refer to the family of ophicordycipitaceae or a species thereof, such as *Ophiocordyceps sinensis* (*O. sinensis*) which was known as *cordyceps sinensis* (*C. sinensis*) prior to 2007. Accordingly, unless indicated to the contrary, the terms *C. sinensis* and *O. sinensis* can be used interchangeably.

As used herein, "*Cordyceps* extract" refers to an extract derived from the raw material of any part of a *cordyceps* organism. In some embodiments, extracts can be made or derived from specific parts of *Cordyceps*, such as the mycelium (i.e. fruiting body such as a mushroom), cells, hyphae, apothecium, hymenium, or spores of the fungus including anamorphic strains, mixtures, etc. Extracts can take the form of a liquid, a concentrated liquid, a powder, or of raw *cordyceps* material in a reduced form, such as sliced, chopped, pulverized, etc. Those of ordinary skill in the art will recognize various available extraction techniques. In one embodiment, a *cordyceps* extract can be obtained by a process as recited in U.S. Pat. No. 7,718,416, which is incorporated herein by reference.

As used herein, "effective amount," "therapeutically effective amount," or "therapeutically effective rate(s)" of an active ingredient, agent, or compound refers to a non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "extract" includes any parts of, or a material derived from, the raw material of a particular source. Extracts may take many forms including but not limited to: solid, liquid, powder, particulate, chopped, distillate, etc. and may be performed by any number of procedures or protocols, such as chopping, grinding, pulverizing, boiling, steaming, soaking, steeping, applying a gas, etc., and may employ any suitable reagents, such as water, alcohol, steam, or other organic materials. A wide number of extraction methods and techniques are known to those of ordinary skill in the art. In some embodiments, extracts can be made from specific parts of a source. In some aspects an extract may include one or more active constituents or active agents.

As used herein, a "liquid extract" refers to those substances prepared using a solvent, e.g., ethanol, water, steam, superheated water, methanol, hexane, chloroform liquid, liquid $CO_2$, liquid $N_2$, propane, supercritical $CO_2$ or any combination thereof. Liquid extractions can result in a liquid, suspension, slurry, particulate, dried powder or other solid or semi-solid forms derived from a source when using a liquid extract as a step in the overall extraction protocol. Liquid extracts typically have a given purity percentage and can be relatively to highly pure. In some aspects, the purity of an extract can be controlled by, or be a function of the extraction process or protocol.

As used herein, "excipient" refers to a substantially inert substance, which may be combined with an active agent and a carrier to achieve a specific dosage formulation for delivery of the active agent to a subject, or to provide a dosage form with specific performance properties. For example, excipients may include binders, lubricants, etc., but specifically exclude active agents and carriers.

As used herein, "formulation" and "composition" can be used interchangeably and refer to a combination of at least two ingredients. In some embodiments, at least one ingredient may be an active agent or otherwise have properties that exert physiologic activity when administered to a subject.

As used herein, "skin" refers to an organ of a subject's integumentary system that includes ectodermal tissue, typically in layers such as epidermis and dermis, and in some embodiment also the hypodermis. Various skin types and conditions specific to individual species are well known. In one embodiment, the skin may be mammalian skin. In a more specific embodiment, the skin may be human skin.

When referring to the achievement of an effect, phrases such as "reduction in appearance of," "reducing the appearance of," or "diminishes the appearance of," one or more condition(s) or features refers to a visibly measurable reduction in the condition(s). In some embodiments, the reduction may be noticeable to the naked eye. In some instances, the reduction includes a reduction as measured using digital imaging such as, light optical profilometry, corneometers, cutometers, or ultrasound. Changes in other physical parameters or properties, such as elasticity, hydration, lipid content and distribution, and cellular retention may also be measured using various known techniques and used as an indicator of an achievement of an effect. Achievement of an effect, such as a reduction, can take place after a single treatment or can occur over a period of time. For example, the appearance of the reduction can be measured from a subject's appearance prior to, or at commencement (e.g. on day 1) of a treatment and extending over a period of time during which treatment continues according to a prescribed or selected regimen, e.g., 1 week, 2 weeks, 3 weeks, 1 month, 2 months, 3 months, 1 year, etc. The amount of effect achieved, such as degree of reduction can vary based on a variety of factors, including but not limited to, the skin type of the subject, the skin condition that is being treated, and/or the individual characteristics of the subject.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

The terms "treat," "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, stabilizing (i.e. not worsening) the state of a condition, delaying or slowing progression, amelioration or palliation of the condition, and diminishment of the reoccurrence of condition, whether detectable or undetectable. "Treat," "treating" and "treatment" can also mean prophylactic. Such prophylactic treatment can also be referred to as prevention or prophylaxis of a condition. The prophylaxis may be partial or complete. Partial prophylaxis may result in the delayed onset of a physiological condition.

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

Comparative terms such as "more effectively," "greater than," "improved," "enhanced," "decreased," "increased," and like terms can be used to state a result achieved or property present in a formulation or process that has a measurably better or more positive outcome than the thing to which comparison is made. In some instances comparison may be made to the prior art.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Any steps recited in any method or process claims may be executed in any order and are not limited to the order presented in the claims unless otherwise stated.

The present inventors have discovered numerous skin benefits that can be achieved through application and use of topical formulations that include a *Cordyceps* extract. Such benefits can include without limitation, reduced presence and visibility of fine lines and wrinkles, improved skin elasticity and hydration, improved color, and improved texture and skin tone among others. Also discovered is the importance of the specific content of the *Cordyceps* extract used in the topical formulations. Further discovered is the value of a routine or regimen in guiding application and use of the topical formulation.

Accordingly, in one invention embodiment there is provided a *Cordyceps* extract having either a mannitol concentration of from about 1 wt % to about 25 wt % or an adenosine concentration from about 0.1 wt % to about 5 wt % of the extract. In one embodiment, the mannitol content can be from about 5 wt % to about 15 wt % of the extract. In another embodiment, the mannitol content can be from about 1 wt % to 10 wt % of the extract. In yet another embodiment, the mannitol content can be from about 5 wt % to about 20 wt % of the extract.

In one embodiment, the adenosine content can be from about 0.2 wt % to about 2.0 wt % of the extract. In another embodiment, the adenosine content can be from about 0.5 wt % to about 3 wt % of the extract. In yet another embodiment, the adenosine content can be from about 1 wt % to about 5 wt % of the extract.

In some embodiments, the extract can have a mannitol content that can be from about 5 wt % to about 15 wt % and an adenosine content can be from about 0.25 wt % to about 2.0 wt % of the extract. In other embodiments, the extract can have a mannitol content that can be from about 5 wt % to about 10 wt % and an adenosine content can be from about 1.0 wt % to about 2.0 wt % of the extract.

Various *Cordyceps* species can be used as the extract source. However, in one aspect, the *Cordyceps* extract can be derived from a member selected from the group consisting of: *O. sinensis, C. sinensis, C. militaris, C. ophioglossoides, C. capita, C. pseudomilitaris*, and *C. cardinalis*, and combinations thereof. In one embodiment, the *Cordyceps* extract is derived from *C. militaris*. In another embodiment, the *Cordyceps* extract is derived from *C. sinensis*. In yet another embodiment, the *Cordyceps* extract is derived from *C. ophioglossoides*. The extract can be derived from any part of the *Cordyceps* fungus as previously mentioned. In one embodiment, the extract can be derived from whole ground mushrooms.

In one embodiment, the mannitol content in the extract can be greater than about 5 wt %. In another embodiment the amount can be from about 5 wt %, to about 20 wt % of the extract. In another embodiment, the adenosine content in the extract can be greater than about 0.5 wt %. In yet another embodiment the amount can be from about 0.5 wt % to about 3 wt %. The extract can take various forms and be a liquid extract, a powder extract, a compound, or a mixture thereof. In some embodiments, the extract can be soluble in water.

Also presented herein, are topical formulations that include a *Cordyceps* extract. In some embodiments, the topical formulation can include a pharmaceutically acceptable carrier and can have a mannitol concentration of at least about 5 wt % or an adenosine concentration of at least about 0.25 wt %. In one embodiment, the mannitol content is at least about 7 wt %. In another embodiment, the mannitol content is at least about 10 wt %. In one embodiment, the adenosine content is at least about 0.50 wt %. In another embodiment, the adenosine content is at least about 1 wt %. In some embodiments, the extract can have a mannitol content of at least about 5 wt % and an adenosine content of at least about 0.25 wt %. In other embodiments, the extract can have a mannitol content is at least about 7 wt % and an adenosine content is at least 0.5 wt %.

The concentration of the *Cordyceps* extract in the formulation can vary. In one embodiment, the extract can be present in the formulation in an amount of from about 0.10 wt % to about 2.0 wt % of the total formulation. In another embodiment, the *Cordyceps* extract can be present in the formulation in an amount of from about 0.5 wt % to about 5 wt % of the total formulation. In yet another embodiment, the *Cordyceps* extract can be present in the formulation in an amount of about 1 wt % of the total formulation. In another embodiment the *Cordyceps* extract can be present in the formulation in an amount of from about 0.01 wt % to about 65 wt %. The *Cordyceps* extract can take any form as described herein.

A wide variety of pharmaceutical carriers that are suitable for preparation of a topical formulation can be included in the present formulations. The pharmaceutically acceptable carrier can be physiologically inert and non-toxic. In some embodiments, the pharmaceutically acceptable carrier can be a pharmaceutical grade compound. The pharmaceutically acceptable carrier can include a volatile solvent, a non-volatile solvent, and/or a thickener. In one embodiment the pharmaceutically acceptable carrier can include a preservative and/or an odorant.

A number of suitable volatile solvents or solvent components can be used and can aid in maintaining the formulation in a desired physical form prior to application to the skin. In one embodiment, the volatile solvent can be included in the formulation in an amount of greater than about can comprise at least one of denatured alcohol, ethanol, hexane, methyl ethyl ketone, methanol, propanol, isobutene, pentane, water, and combinations thereof. In another embodiment, the volatile solvent can comprise water. In one embodiment, the water can be deionized. In one embodiment, the volatile solvent or solvent component can comprise greater than about 40 wt %, 70 wt %, 75 wt %, 80 wt %, 85 wt %, 90 wt % or even greater than 95 wt % of the total formulation. In one embodiment, the volatile solvent comprise from about 40 wt % to about 95 wt % of the formulation.

A variety of non-volatile solvents can be utilized in the present formulations and can aid in loading of active agents or active fractions into the formulation and maintaining such agents or fractions in a solubilized form that is suitable for topical administration and absorption. Additionally, such solvents can aid in enhancing penetration of the active agents or fractions into the skin. The non-volatile solvent can be selected from the group consisting of butylene glycol, propanediol, propylene glycol, isoprene glycol, pentylene glycol, glycerol, sorbitol, polyethylene glycol, polypropylene glycol, other polyols, other sugar alcohols, and combinations thereof. In another embodiment, the non-volatile solvent comprises PEG-4. In yet another embodiment, the non-volatile solvent comprises butylene glycol. The amount of non-volatile solvent will vary based on the actual formulation. However in one embodiment, the non-volatile solvent can comprise from about 1 wt % to about 20 wt % of the total formulation. In another embodiment, the non-volatile solvent can comprise from about 1 wt % to about 10 wt % of the formulation. In yet another embodiment, the non-volatile solvent can comprise from about 1 wt % to about 5 wt % of the total formulation. In one embodiment, the non-volatile solvent can be present in an amount of about 4 wt % of the formulation.

Thickeners or thickening agents are useful in preparing a topical formulation with a desired viscosity which can affect the ease of use and application to the skin as well as the rate at which the ski absorbs the formulation. The thickener can be a member selected from the group consisting of acrylate/C10-C30 alkyl acrylate cross polymer, Carbomer, polyacrylamide, polyacrylate-13, acrylate copolymers, sodium polyacrylate, taurate copolymer derivatives, xanthum gum, carrageenan, guar gum, sclerotium gum, cellulose gum, hydroxypropylcellulose, methylcellulose, hydroxypropyl methylcellulose, cetyl hydroxyethylcellulose, hydrocolloids, and combinations thereof. In one embodiment, the thickener can be an acrylate/C10-C30 alkyl acrylate cross polymer, commercially known as Carbopol® Ultrez 20A (available from Lubrizol Corp.). In another embodiment, the thickener can be Carbomer. The thickener can be present in an amount of from about 0.1 wt % to about 10 wt % of the total formulation. In one embodiment, the thickener can comprise up to about 1 wt %, 2 wt %, 3 wt %, 4 wt %, 5 wt %, 6 wt %, or 7 wt % of the total formulation. In some embodiments, the thickener can comprise up to about 5 wt % of the total formulation.

Preservatives or preserving agents play the role of adding stability and increasing shelf life of the formulation. While optional, when present, the preservative in the topical formulation can include any pharmaceutically acceptable preservative. In some embodiments, the preservative will be selected from the group consisting of benzyl alcohol, EDTA, 1,2-hexanediol, caprylyl glycol, potassium sorbate, sodium benzoate, and combinations thereof. In one embodiment, the preservative is sodium benzoate. In another embodiment, the preservative is 1,2-hexanediol caprylyl glycol. In some embodiments, the preservative can be present in an amount of up to about 0.5 wt %, 1 wt %, 2 wt %, 3 wt %, 4 wt %, or 5 wt % of the total formulation.

Odorants and fragrances can also be ingredients included in the present formulations. Such ingredients typically add to the pleasant use of the formulation. Because topical formulations are applied to the skin, the smell of the formulation lingers for a considerable amount of time. As such, formulations that are malodorous can deter a subject from using them in the proper frequency or amount. Conversely, when a formulation has a pleasant smell it may incentivize the subject to apply the formulation regularly and liberally. This is particularly true when formulations are applied to the subject's face which is in close proximity to the subject's olfactory sense. The odorant can be any desired fragrance. In some embodiments, the fragrance can be used to mask the odor of the *Cordyceps* extract. In other embodiments, the fragrance can be added to enhance the experience of the user. In certain embodiments, the fragrance or odorant can comprise up to about 5 wt % of the total formulation. In one embodiment, the fragrance or odorant can comprise up to about 2 wt % of the total formulation.

As needed or desired, the present formulations can include a pH adjuster. The pH adjuster can be any ingredient that is suitable for application to a subject's skin without causing damage from the acid or alkaline environment created at the location of topical application. pH adjusters can be either acidic or alkaline. In some embodiments, the pH adjuster can be selected from the group consisting of citric acid, lactic acid, sodium hydroxide, and triethanolamine. In one example, the pH adjuster is sodium hydroxide. The pH of the formulation can range from about 5 to about 8. In one exemplary embodiment, the pH ranges from about 5 to about 6.

In certain embodiments, the formulation can comprise additional ingredients. In some embodiments the additional ingredients can be an active and/or a non-active type. Exemplary additional ingredients can include at least one of: dimethylethanolamine (DMAE), alpha lipoic acid, hyaluronic acid, alpha hydroxy acid, vitamin A, vitamin C, vitamin E, aloe jelly, argan oil, cocoa butter, shea butter, other ingredients typically found in cosmetic formulations, and combinations thereof. The additional ingredients in the formulation can be selected by one of ordinary skill in the art in order to achieve a formulation with specific properties and performance.

In one specific embodiment, the topical formulation can comprise a *Cordyceps* extract in an amount of about 0.5 wt % to about 5 wt %, water in an amount of at least about 90 wt %, butylene glycol in an amount of about 1 wt % to 10 wt %, and a C10-C30 alkyl acrylate cross polymer in an amount of about 0.1 wt % to about 5 wt %. In one embodiment of the before mentioned formulation, the *Cordyceps* extract can be derived from *C. sinensis*.

The topical formulation can include a variety of active constituents. In one embodiment, the active constituents or fractions in the formulation can comprise a member selected from the group consisting of: uridine, uracil, adenine, adenosine, inosine, cordycepin, and mannitol. The active constituents can be equal to or smaller than 1,000 daltons in size.

Further presented herein are methods of treating a dermatological condition. One exemplary method can comprise providing a *Cordyceps* extract and administering a therapeutically effective amount of the extract to the skin of a subject. In some embodiments, the extract can be administered as a formulation containing the *Cordyceps* extract. The *Cordyceps* extract and formulation can be as recited herein. The dosage amount required to be a therapeutically effective amount can be selected to accommodate the needs of a specific subject or indication. In some embodiments, the effect of the treatment on the dermatological condition can be about a 5% reduction, 10% reduction, 15% reduction, 20% reduction, 25% reduction, 30% reduction, 35% reduction, 40% reduction, 45% reduction, or a 50% reduction in the appearance, presence, or severity of an undesired dermatological condition. In some embodiments the effect of the treatment on a dermatological condition can also be about a 5% increase, 10% increase, 15% increase, 20% increase, 25% increase, 30% increase, 35% increase, 40% increase, 45% increase, or a 50% increase in the appearance of a desired dermatological condition. Again, such results can be measured and quantified by the mechanisms recited herein.

In one embodiment, the formulation can be used to treat a dermatological condition selected from the group consisting of: fine lines, wrinkles, mottled pigmentation, skin spots, uneven skin tone, tactile roughness/smoothness, and firmness in appearance. In one embodiment, a subject can experience at least about a 20% reduction in the appearance of fine lines and the wrinkles, mottled pigmentation, and uneven skin tone when clinically graded. In another embodiment, a subject can experience at least about a 15% increase in the overall firmness of the skin when clinically graded. In yet another embodiment, a subject can experience at least about a 35% increase in overall smoothness of the skin when clinically graded.

In another embodiment, the dermatological condition is crow's feet. In one embodiment, a subject can experience at least about a 50%, reduction in the appearance of crow's feet, based on a subject's self assessment.

In yet another embodiment, the dermatological condition is selected from the group consisting of pore size, radiance, overall skin appearance, skin moisture content, skin tone evenness, and skin density/thickness. In one embodiment, a subject can experience at least about a 20% reduction in the appearance of pore sizes when clinically graded. In another embodiment, a subject can experience at least about a 25% increase in the overall radiance when clinically graded. Exemplary improvements as graded by a clinical grader in a variety of dermatological conditions are shown in FIG. 1.

The exact improvement in the dermatological condition can vary based on the subject or user and the treatment regimen. In one embodiment, the treatment regimen can include topically applying or administering the formulation to a skin surface of a subject once a day, twice a day, or three times a day. Such application or administration can be at a target sight on the skin where or near where the dermatological condition is located, or likely or anticipated to be located. In another embodiment, the method can include topically applying the formulation to the skin surface once a week, twice a week, three times a week, every other day, or daily. This process can be carried out indefinitely, or until the desired result is achieved. For example, the treatment may be carried out for 1 week, 2 weeks, 3 weeks, 1 month, 3 months, 1 year, or more. In one example, the formulation can be applied to an area of the skin twice daily for a period of at least one week. In another embodiment, the formulation can be applied twice daily for a period of at least four weeks. In yet another embodiment, the formulation is applied twice daily for a period of at least eight weeks. In a further embodiment, the formulation is applied twice daily for a period of at least twelve weeks.

The results obtained by application of the extracts and formulations recited herein can also be measured in terms of gene expression in some embodiments. Accordingly, methods for modulating gene expression in a subject, or of determining the effectiveness of a treatment or treatment regimen are also encompassed by the present technology. A method of modulating gene expression can include administering *Cordyceps* extract or a formulation containing such to an area of skin in an amount sufficient to modulate gene expression activity. Modulation can be an increase, or decrease in gene activity. Modulation can also be initiation of gene expression. In one embodiment, application of the extract or formulation can modulate expression of a gene selected from the group consisting of: ICAM1, CCL5, IGFBP3, SMAD7, VEGFA, KLK5, KLK7, SOD2, and IGFBP3. In one example, applying an exemplary formulation can result in a 5 fold increase in the expression of the ICAM1 gene. ICAM1 is an adhesion protein that binds to hyaluronan and stimulates the inflammatory immune responses in the skin. In another example, applying an exemplary formulation can result in a 7 fold increase in the expression of the CCL5 gene. CCL5 is a chemokine that is involved in improving wound healing. In yet another example, applying an exemplary formulation can result in a 3 fold change in the expression of the IGFBP3 gene. IGFBP3 along with IGF-1 has been found to be associated with a decrease in facial aging and skin wrinkling. In a further example, applying an exemplary formulation can result in a 2.5 fold increase in expression of the SMAD7 gene. SMAD7 stimulation is associated with increased keratinocyte proliferation. In one embodiment, applying an exemplary formulation can result in a 2 fold increase in expression of the VEGFA gene. VEGFA is a vasodilator that improves skin radiance. In another embodiment, applying an exemplary formulation can result in a 1.5 fold decline in expression of the KLK5 gene. In yet another embodiment, applying an exemplary formulation can result in a 1 fold decline in expression of the KLK7 gene. KLK5 and KLK7 are serine proteases that regulate the skin peeling process and cleave cellular adhesion proteins. In a further example, applying an exemplary formulation can result in a 2 fold increase in expression of the SOD2 gene. SOD2 protects against oxidative stress and could prevent hyper-pigmentation. In some embodiments, gene ontology analysis demonstrates that applying exemplary formulations can result in physiological improvements in the skin's overall condition.

Exemplary formulations can also stimulate certain growth factors and in one embodiment a method of stimulating growth factors is presented. Such a method can include administering a therapeutically effective amount of a *Cordyceps* extract or formulation containing such to an area of skin. In one embodiment, the growth factors stimulated can be selected from the group consisting of INHBA, HGF, GDNF, BTC, EREG, IL11, GDF15, BMP2, BDNF, FGF2, CSF2, CSF3, CXCL1, BMP6, and NRG1.

The present disclosure also encompasses methods of evaluating effectiveness of a *Cordyceps* extract or formulation as a treatment for a skin condition. Such a method can include identifying one or more genetic markers associated with a specific skin or dermatological condition, applying a *Cordyceps* extract or formulation to a portion of skin containing the dermatological condition, and measuring modulation of expression of the one or more gene markers following application of the *Cordyceps* extract or formulation. Subsequently, the extract or formulation can be adjusted in content or dosage in view of the gene expression achieved. In some embodiments, measurements of gene expression can be made over time in order to establish a dosage regimen which maximizes effectiveness of treatment of the skin condition.

Further presented herein are methods of preparing a *Cordyceps* extract having a mannitol concentration of at least 5 wt % or an adenosine concentration of at least 0.25 wt %, or both. Such a method can comprise reducing a source of *Cordyceps* to a particulate form and partitioning active constituents from the particulate form by solvent extraction. In one example the solvent is water and the extraction temperature ranges from about 50° C. to about 150° C. Following extraction, the water can be removed from the active constituents leaving behind a dehydrated *Cordyceps* extract. The *Cordyceps* extract can be freeze, air, or spray dried to create a powder. In some embodiments, the source of the *Cordyceps* used in the method can be *Cordyceps sinensis*. The extract can be as previously described.

Moreover presented herein are methods of preparing topical *Cordyceps* formulations and dosage forms. Such a method can include providing a *Cordyceps* extract as recited herein and combining the *Cordyceps* extract with a volatile solvent, a non-volatile solvent, and a thickener. The method can further comprise mixing the formulation with a preservative, odorant, or other ingredients. The formulation can be as described above.

Embodiments of the present disclosure will be described with reference to the following Examples which are provided for illustrative purposes only and should not be used to limit the scope of or construe the invention.

EXAMPLES

Example 1

Transdermal/Topical Delivery Formulations

Formulations were prepared according to embodiments of the present disclosure utilizing compositional components set forth in Tables 1A and 1B. Each of the formulations was prepared in a batch size of 4,300 grams. All raw materials were stored at ambient conditions prior to manufacturing the formulations. The ingredients listed in Tables 1A and 1B were added to the mixture one at a time, in the order presented below, and the mixture was blended by hand following each addition.

TABLE 1A

Example Control Formulation

| Ingredient | Grams added | Wt. % |
|---|---|---|
| Water | 4,046.00 | 94.05 |
| Versene ™ Na2 Crystals* | 2.15 | 0.05 |
| Carbopol ® Ultrez 20A* | 21.50 | 0.50 |
| Butylene Glycol | 172.00 | 4.00 |
| Sodium Benzoate | 8.60 | 0.20 |
| Symdiol ® 68* | 43.00 | 1.00 |
| Fragrance Dewy Skin | 8.60 | 0.20 |
| Total | 4,301.85 | 100.00 |
| 50% Sodium Hydroxide** | 7.25 | — |

*Versene ™ Na2 Crystals is available from Akzo Nobel; Carbopol ® Ultrez 20A is available from Essential Ingredients, Inc.; and Symdiol ® 68 is available from Symrise AG.
**The 50% sodium hydroxide solution was added to adjust the pH of the formulation from 4.263 to 5.359.

TABLE 1B

Example Active Formulation

| Ingredient | Grams added | Wt. % |
|---|---|---|
| Water | 4,002.00 | 93.05 |
| Versene ™ Na2 Crystals* | 2.16 | 0.05 |
| Carbopol ® Ultrez 20A* | 21.49 | 0.50 |
| Butylene Glycol | 172.05 | 4.00 |
| Sodium Benzoate | 8.60 | 0.20 |
| Symdiol ® 68* | 43.00 | 1.00 |
| Cordyceps Extract | 43.00 | 1.00 |
| Fragrance Dewy Skin | 8.59 | 0.20 |
| Total | 4,300.89 | 100.00 |
| 50% Sodium Hydroxide** | 9.47 | — |

*Versene ™ Na2 Crystals is available from Akzo Nobel; Carbopol ® Ultrez 20A is available from Lubrizol, Corp.; Symdiol ® 68 is available from Symrise AG.
**The 50% sodium hydroxide solution was added to adjust the pH of the formulation from 4.396 to 5.463.

The Control and Active Formulations were tested for initial viscosity using a viscometer set at 1.5 rpms. The Control Formulation was 176,000 cps. The Active Formulation was 30,200 cps. In addition, the general appearance of the formulations was noted. The Control Formulation was a colorless gel. The Active Formulation was an orange opaque gel.

Examples 2-4

Clinical Study

A single-center, double blind, clinical trial was conducted to assess and compare the efficacy of the Active Formulation to the Control Formulation. A total of 67 women with self-perceived dry facial skin completed the study; 35 of the participants were given the Active Formulation and 32 of the participants were given the Control Formulation. The participants were instructed to apply the topical formulation to the entire face twice daily, once in the morning and once in the evening, after washing. In addition, participants were instructed to keep daily diaries to record product application times and comments.

Clinical evaluations of the participants were conducted during the initial visit, at 1 week, 4 weeks, 8 weeks, and 12 weeks. Prior to each clinical evaluation, participants were acclimated to ambient temperatures and humidity for at least 15 minutes. The waiting rooms were maintained at a temperature range between 68° F. to 76.5° F. and a relative humidity from about 35% to about 48%. The clinical evaluations included five tests. Specifically the participants were tested in the areas of (1) self-assessment questionnaires, (2) digital imaging using the VISTA-CR (Canfield Scientific, Inc.), (3) skin hydration measurements using the Corneometer® CM 825 (Courage+Khazaka electronic GmbH), (4) elasticity measurements using a Cutometer® dual MPA 580 (Courage+Khazaka electronic GmbH), at weeks 8 and 12 only, and (5) density and skin thickness measurements using a 50 MHz ultrasonic transducer interfaced with a DUB® 6100 OEM System (Taberna Pro Medicum GmbH).

Example 2

Self-Assessment Questionnaire Results

Self-assessment questionnaires were completed by the participants at baseline, and weeks 4, 8, and 12. The questionnaires included assessment questions in the areas in the skin attributes, improvements in wrinkles, overall product attributes, overall opinions, and tolerability. The skin attribute questions specifically asked about overall skin firmness, skin firmness around the eyes, skin smoothness, skin tone, skin brightness, the appearance of skin spots, noticeability of pores/pore size, skin hydration, and skin softness. The questions regarding wrinkle improvements were focused on different areas of the face including smile/frown fines and crow's feet. The questions regarding overall product attributes asked the participant's opinion regarding the overall product, the ease of application, compatibility with make-up, and mildness/gentleness of the formulation. The overall opinion questions focused on the overall experience, speed of effects, breadth of effects, and skin feel and appearance in the areas of younger looks and health. The questionnaires were completed by the participants while looking in a mirror. The results in percent improvement over baseline are included in the tables below. The percent of improvement over baseline was calculated using the general formulation, Percent Improvement over Baseline =

$$\frac{(\text{Self Assessment Scores})}{\text{Self Assessment Baseline Scores}} \times 100$$

TABLE 2A

Overall Skin Firmness - % Improvement

| Formulation | 1 week | 4 weeks | 8 weeks | 12 weeks |
|---|---|---|---|---|
| Control Formulation | 1.90 | 11.50 | 18.40 | 18.20 |
| Active Formulation | 15.90 | 30.30 | 26.90 | 41.60 |

TABLE 2B

Skin Firmness Around Eyes - % Improvement

| Formulation | 1 week | 4 weeks | 8 weeks | 12 weeks |
|---|---|---|---|---|
| Control Formulation | 14.30 | 30.20 | 36.50 | 39.60 |
| Active Formulation | 25.20 | 35.50 | 37.30 | 54.30 |

TABLE 2B-continued

Skin Firmness Around Eyes - % Improvement

| Formulation | 1 week | 4 weeks | 8 weeks | 12 weeks |
|---|---|---|---|---|

TABLE 2C

Skin Smoothness - % Improvement

| Formulation | 1 week | 4 weeks | 8 weeks | 12 weeks |
|---|---|---|---|---|
| Control Formulation | 3.70 | 16.40 | 20.90 | 26.70 |
| Active Formulation | 17.50 | 33.00 | 28.80 | 36.00 |

TABLE 2D

Skin Tone/Evenness - % Improvement

| Formulation | 1 week | 4 weeks | 8 weeks | 12 weeks |
|---|---|---|---|---|
| Control Formulation | 8.80 | 18.30 | 31.10 | 38.00 |
| Active Formulation | 17.60 | 35.10 | 35.30 | 49.00 |

TABLE 2E

Skin Brightness - % Improvement

| Formulation | 1 week | 4 weeks | 8 weeks | 12 weeks |
|---|---|---|---|---|
| Control Formulation | 13.00 | 29.30 | 30.00 | 45.70 |
| Active Formulation | 21.80 | 32.70 | 35.40 | 50.60 |

TABLE 2F

Appearance of Skin Spots/Discoloration - % Improvement

| Formulation | 1 week | 4 weeks | 8 weeks | 12 weeks |
|---|---|---|---|---|
| Control Formulation | 11.20 | 25.00 | 41.20 | 39.10 |
| Active Formulation | 18.80 | 28.20 | 36.30 | 47.00 |

TABLE 2G

Noticeability of Pores/Pore Size - % Improvement

| Formulation | 1 week | 4 weeks | 8 weeks | 12 weeks |
|---|---|---|---|---|
| Control Formulation | 6.20 | 10.00 | 37.80 | 33.30 |
| Active Formulation | 1.90 | 20.10 | 22.00 | 38.80 |

TABLE 2H

Skin Hydration - % Improvement

| Formulation | 1 week | 4 weeks | 8 weeks | 12 weeks |
|---|---|---|---|---|
| Control Formulation | 16.30 | 27.30 | 42.00 | 44.50 |
| Active Formulation | 39.00 | 54.20 | 42.20 | 57.00 |

TABLE 2I

Skin Softness - % Improvement

| Formulation | 1 week | 4 weeks | 8 weeks | 12 weeks |
|---|---|---|---|---|
| Control Formulation | 5.50 | 6.60 | 15.90 | 24.90 |
| Active Formulation | 17.20 | 26.60 | 19.70 | 28.60 |

Figure 2:
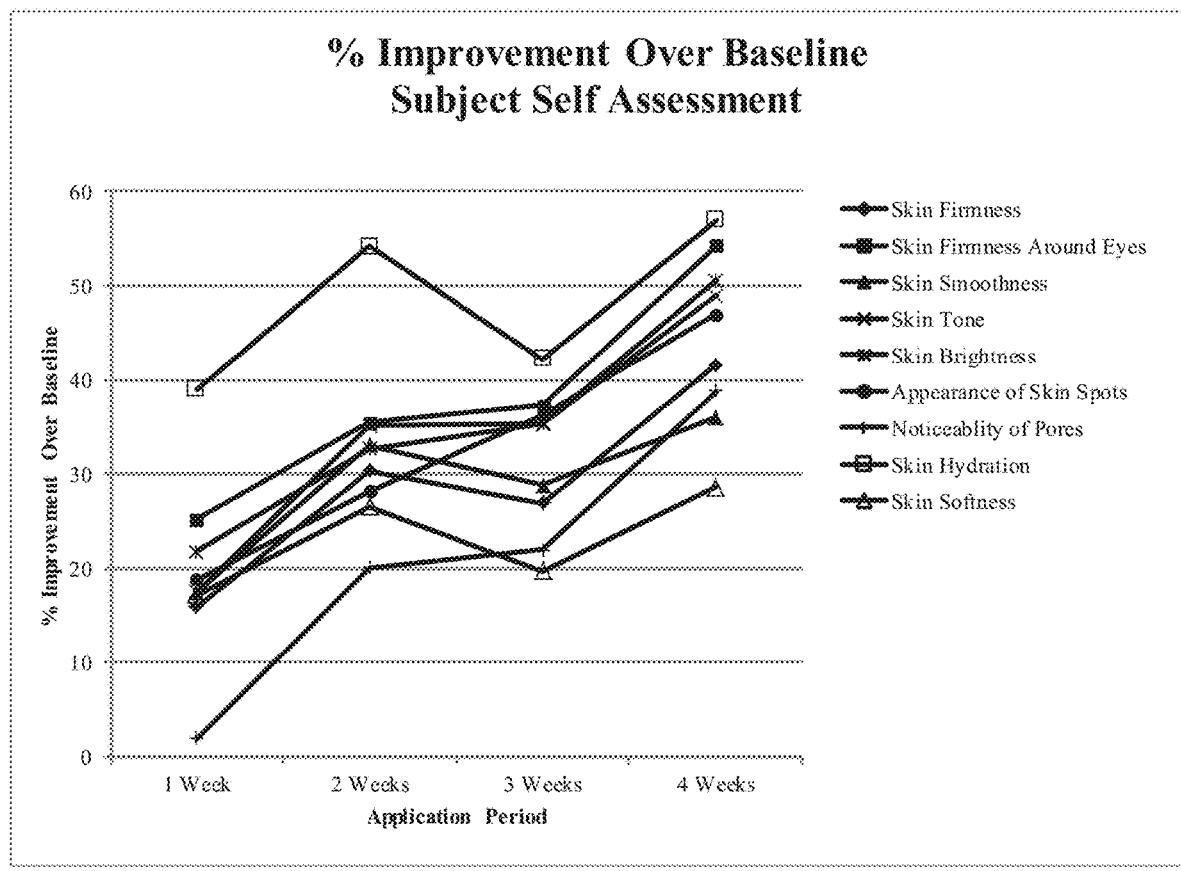
FIG. 2 shows subject reported self-assessment results for percent improvement over baseline of a variety of treated dermatological conditions following the application of a topical formulation that includes a *Cordyceps* extract.

FIG. 2 shows the percent improvement over baseline of the active formulation for the above dermatological conditions based on the user's self assessment.

Example 3

Clinical Grader Results

Clinical grader testing was performed using various instrumentations and protocols as stated below.

Digital Imaging

Digital imaging of each of the participants was taken at baseline and weeks 4, 8, and 12 using the VISTA-CR (Canfield Scientific, Inc.). VISTA-CR is an imaging device designed to enhance the visualization of skin features including wrinkles, fine lines, skin texture, coloration/evenness, photo damage, vascular features, and porphyrins (*P. acnes*). Each of the images were analyzed using raking light optical profilometery in Image-Pro® Plus software (Media Cybernetics, Inc.). This software detects the count, length (mm), width (mm), area (mm$^2$) and depth of wrinkles. Higher values indicated more sever wrinkles; whereas, lower values were indicative of improvement/less severe wrinkles. The ranking light images were analyzed for wrinkle parameters in the crow's foot area under both eyes.

Cutometer

Skin elasticity measurements were taken of each participant at baseline and weeks 8 and 12 using the Cutometer® dual MPA 580 (Courage+Khazaka electronic GmbH). The Cutometer® measures elasticity of the uppermost skin layer using negative pressure to deform the skin. Skin is drawn into the aperture of the probe and after a defined amount of time released again. The penetration depth is determined inside the probe using an optical measuring system in which the light intensity varies due to the penetration depth of the skin. Cutometer measurements were taken on the right ocular bone of each participant.

Density and Skin Thickness Measurements—Ultrasound

Ultrasound measurements of each of the participants were taken at baseline and weeks 4, 8, and 12 using a 50 MHz ultrasonic transducer interfaced with a DUB® 6100 OEM System (Taberna Pro Medicum). This high frequency ultrasound imaging system allows for measurements of skin thickness, epidermis thickness, and skin density at a maximum penetration of 4 mm and an axial resolution of 31 μm. The measurements were taken from the left crow's foot area of each participant.

TABLE 3A

Overall Skin Firmness - % Improvement

| Formulation | 1 week | 4 weeks | 8 weeks | 12 weeks |
|---|---|---|---|---|
| Control Formulation | 0.00 | 1.00 | 3.50 | 3.90 |
| Active Formulation | 0.00 | 6.60 | 11.90 | 15.80 |

TABLE 3B

Reduction of Fine Lines & Wrinkles - % Improvement

| Formulation | 1 week | 4 weeks | 8 weeks | 12 weeks |
|---|---|---|---|---|
| Control Formulation | 0.30 | 3.00 | 4.60 | 7.70 |
| Active Formulation | 0.60 | 7.30 | 13.10 | 20.80 |

TABLE 3C

Tactile Roughness/Skin Smoothness - % Improvement

| Formulation | 1 week | 4 weeks | 8 weeks | 12 weeks |
|---|---|---|---|---|
| Control Formulation | 5.80 | 4.60 | 15.00 | 23.20 |
| Active Formulation | 9.50 | 19.00 | 28.50 | 39.00 |

TABLE 3D

Skin Tone/Evenness - % Improvement

| Formulation | 1 week | 4 weeks | 8 weeks | 12 weeks |
|---|---|---|---|---|
| Control Formulation | 0.00 | 2.40 | 5.30 | 11.00 |
| Active Formulation | 0.30 | 6.20 | 3.40 | 21.80 |

TABLE 3E

Skin Radiance - % Improvement

| Formulation | 1 week | 4 weeks | 8 weeks | 12 weeks |
|---|---|---|---|---|
| Control Formulation | 0.90 | 5.60 | 6.90 | 13.10 |
| Active Formulation | 1.90 | 9.70 | 17.50 | 27.00 |

TABLE 3F

Appearance of Skin Spots/Discoloration (Mottled Pigmentation) - % Improvement

| Formulation | 1 week | 4 weeks | 8 weeks | 12 weeks |
|---|---|---|---|---|
| Control Formulation | 0.30 | 0.90 | 3.00 | 5.00 |
| Active Formulation | 0.00 | 5.50 | 15.70 | 22.00 |

TABLE 3G

Noticeability of Pores/Pore Size - % Improvement

| Formulation | 1 week | 4 weeks | 8 weeks | 12 weeks |
|---|---|---|---|---|
| Control Formulation | 0.00 | 0.40 | 2.00 | 2.10 |
| Active Formulation | 0.00 | 7.20 | 15.40 | 23.10 |

TABLE 3H

Overall Appearance - % Improvement

| Formulation | 1 week | 4 weeks | 8 weeks | 12 weeks |
|---|---|---|---|---|
| Control Formulation | 0.00 | 2.60 | 3.90 | 9.40 |
| Active Formulation | 1.50 | 8.60 | 16.30 | 24.00 |

FIG. 1 shows the percent improvement over baseline of the active formulation for the above dermatological conditions based on the clinical grader's assessment.

Example 4

Skin Hydration Measurements—Corneometer® CM 825 MPA 580

Skin hydration measurements were taken of each participant at baseline and weeks 4, 8, and 12 using the Corneometer® CM 825 (Courage+Khazaka electronic GmbH). The Corneometer® measures the change in the dielectric constant due to skin surface hydration changing the capacitance of a precision capacitor. The measurement can detect slight changes in hydration level and is not influenced by substances in or on the skin. The measurement depth is 10-20 μm of the stratum corneum. The measurements were taken, in triplicate, at the left ocular bone of each participant. The results of the corneometer testing are shown in Table 4 below.

TABLE 4

Percentage of Subjects that saw Improvement*

| Formulation | 4 weeks | 8 weeks | 12 weeks |
| --- | --- | --- | --- |
| Control Formulation | 2.80 | 24.90 | 6.30 |
| Active Formulation | 5.20 | 16.90 | 0.20 |

*The percent of subjects that saw improvement was calculated using the general formulation, Percentage of subjects that improved =

$$\frac{(\text{number of subjects from baseline}) \times 100}{\text{Total number of subjects}}$$

Twice daily application of the Control and the Active Formulation did not have a significant effect on moisture content of the stratum corneum.

The following examples pertain to further embodiments.

In one example there is a provided, a *Cordyceps* extract having either a mannitol concentration from about 1 wt % to about 25 wt % or an adenosine concentration from about 0.1 wt % to about 5 wt %.

In one example, the mannitol content is from about 5 wt % to about 15 wt %.

In one example, the adenosine content is from about 0.25 wt % to about 2.0 wt %

In one example, the *Cordyceps* extract is derived from a member selected from the group consisting of: *C. sinensis, C. militaris, C. ophioglossoides, C. capita, C. pseudomilitaris*, and *C. cardinalis*, and combinations thereof.

In one example, the *Cordyceps* extract is derived from *C. sinensis*.

In one example, the *Cordyceps* extract is derived from a whole ground mushroom.

In one example, the mannitol content in the *Cordyceps* extract derived from whole ground mushrooms is about 10 wt %.

In one example, the adenosine content in the *Cordyceps* derived from whole ground mushrooms extract is about 1 wt %.

In one example, the mannitol content is from about 5 wt % to about 15 wt % and the adenosine content is from about 0.25 wt % to about 2.0 wt %.

In one example there is provided, a topical formulation comprising a *Cordyceps* extract and a pharmaceutically acceptable carrier, wherein the formulation comprises a mannitol concentration of at least 5 wt % or an adenosine concentration of at least 0.25 wt %.

In one example, the *Cordyceps* extract is present in the formulation in an amount of from about 0.10 wt % to about 2.0 wt %.

In one example, the *Cordyceps* extract is present in the formulation in an amount of about 1 wt %.

In one example, the *Cordyceps* extract is derived from *C. sinensis*.

In one example, the pharmaceutically acceptable carrier comprises:
a volatile solvent;
a non-volatile solvent;
a thickener.

In one example, the pharmaceutically acceptable carrier further comprises preservatives and an odorant.

In one example, the volatile solvent is water.

In one example, water is greater than about 90 wt % of the total formulation.

In one example, the non-volatile solvent is selected from the group consisting of butylene glycol, propanediol, propylene glycol, isoprene glycol, pentylene glycol, glycerol, sorbitol, polyethylene glycol, polypropylene glycol, other polyols, other sugar alcohols, and combinations thereof.

In one example, the non-volatile solvent comprises from about 1 wt % to about 10 wt % of the total formulation.

In one example, the non-volatile solvent is butylene glycol.

In one example, the thickener is a member selected from the group consisting of acrylate/C10-C30 alkyl acrylate cross polymer, Carbomer, polyacrylamide, polyacrylate-13, acrylate copolymers, sodium polyacrylate, taurate copolymer derivatives, xanthum gum, carrageenan, guar gum, sclerotium gum, cellulose gum, hydroxypropylcellulose, methylcellulose, hydroxypropyl methylcellulose, cetyl hydroxyethylcellulose, hydrocolloids, and combinations thereof.

In one example, the thickener comprises up to about 5 wt % of the total formulation.

In one example, the thickener is an acrylate/C10-C30 alkyl acrylate cross polymer.

In one example, the pH of the formulation is from about 5 to 6.

In one example, the formulation includes a pH adjuster.

In one example, the pH adjuster is sodium hydroxide.

In one example, active constituents in the formulation comprises a member selected from the group consisting of: uridine, uracil, adenine, adenosine, inosine, cordycepin, and mannitol.

In one example there is provided, a topical formulation comprising:
a *Cordyceps* extract in an amount of about 0.5 wt % to about 5 wt %;
water in an amount of at least about 90 wt %;
butylene glycol in an amount of about 1 wt % to 10 wt %; and
a C10-C30 alkyl acrylate cross polymer in an amount of about 0.1 wt % to about 5 wt %.

In one example, the *Cordyceps* extract is a *C. sinensis* extract.

In one example there is provided, a method of preparing a *Cordyceps* extract wherein the extract comprises a mannitol concentration of at least 5 wt % or an adenosine concentration of at least 0.25 wt % comprising:
reducing a source of *Cordyceps* to a particulate form;
partitioning active constituents from the particulate form by solvent extraction;

wherein the solvent is water at a temperature from about 50° C. to about 150° C.; and removing the water from the active constituents leaving the *Cordyceps* extract.

In one example of the method, the source of *Cordyceps* can be *Cordyceps* sinensis.

In one example there is provided, a method of preparing a topical *Cordyceps* formulation comprising:

providing a *Cordyceps* extract wherein the extract comprises a mannitol concentration of at least 5 wt % or an adenosine concentration of at least 0.25 wt %; and combining the *Cordyceps* extract with a volatile solvent, a non-volatile solvent, and a thickener.

In one example, the method further comprises combining the formulation with a preservative and an odorant.

In one example of the method, the volatile solvent comprises water.

In one example of the method, the water comprises greater than about 90 wt % of the total formulation.

In one example of the method, the non-volatile solvent is selected from the group consisting of butylene glycol, propanediol, propylene glycol, isoprene glycol, pentylene glycol, glycerol, sorbitol, polyethylene glycol, polypropylene glycol, other polyols, other sugar alcohols, and combinations thereof.

In one example of the method, the non-volatile solvent comprises from about 1 wt % to about 10 wt % of the total formulation.

In one example of the method, the non-volatile solvent is butylene glycol.

In one example of the method, the thickener is a member selected from the group consisting of acrylate/C10-C30 alkyl acrylate cross polymer, Carbomer, polyacrylamide, polyacrylate-13, acrylate copolymers, sodium polyacrylate, taurate copolymer derivatives, xanthum gum, carrageenan, guar gum, sclerotium gum, cellulose gum, hydroxypropylcellulose, methylcellulose, hydroxypropyl methylcellulose, cetyl hydroxyethylcellulose, hydrocolloids, and combinations thereof.

In one example of the method, the thickener comprises up to about 5 wt % of the total formulation.

In one example of the method, the thickener is an acrylate/C10-C30 alkyl acrylate cross polymer.

In one example of the method, the pH of the formulation is from about 5 to 6.

In one example of the method, the formulation includes a pH adjuster.

In one example of the method, the pH adjuster is sodium hydroxide.

In one example there is provided, a method of treating a dermatological condition comprising, topically applying a therapeutically effective amount of a formulation containing a *Cordyceps* extract to an area of skin.

In one example of the method, the dermatological condition is a dermatological condition selected from the group consisting of: fine lines, wrinkles, mottled pigmentation, skin spots, uneven skin tone, tactile roughness/smoothness, and firmness in appearance.

In one example of the method, the dermatological condition is crow's feet.

In one example of the method, the dermatological condition is selected from the group consisting of pore size, radiance, overall skin appearance, skin moisture content, skin tone evenness, and skin density/thickness.

In one example of the method, the dermatological condition is fine lines and wrinkles and overall appearance of the fine lines and the wrinkles decreased by about 20% when clinically graded.

In one example of the method, the dermatological condition is mottled pigmentation and overall appearance of the mottled pigmentation decreased by about 20% when clinically graded.

In one example of the method, the dermatological condition is uneven skin tone and overall appearance in evenness of the skin tone increased by about 20% when clinically graded.

In one example of the method, the dermatological condition is tactile roughness/smoothness of skin and overall smoothness of the skin increased by about 35% when clinically graded.

In one example of the method, the dermatological condition is firmness in appearance and overall the firmness of appearance increased by about 15% when clinically graded.

In one example of the method, the dermatological condition is pore size and the pore size decreased by about 20% when clinically graded.

In one example of the method, the dermatological condition is overall radiance and the overall radiance increased by about 25% when clinically graded.

In one example of the method, the dermatological condition is skin firmness around one's eyes and the skin firmness around one's eyes improved by about 50%, based on a subject's self assessment.

In one example, the method further comprises applying the formulation to an area of the skin twice daily for a period of at least one week.

In one example of the method, the formulation is applied twice daily for a period of at least four weeks.

In one example of the method, the formulation is applied twice daily for a period of at least eight weeks.

In one example of the method, the formulation is applied twice daily for a period of at least twelve weeks.

In one example of the method, the application of the formulation causes expression of a gene selected from the group consisting of: ICAM1, CCL5, IGFBP3, SMAD7, VEGFA, KLK5, KLK7, SOD2, and IGFBP3.

In one example presented herein is a method of modulating gene expression by topically applying a formulation comprising an aqueous *Cordyceps* extract, wherein the genes expressed are selected from the group consisting of: ICAM1, CCL5, IGFBP3, SMAD7, VEGFA, KLK5, KLK7, SOD2, and IGFBP3.

In one example of the method, applying the formulation results in a 5 fold change in the expression of the ICAM1 gene.

In one example of the method, applying the formulation results in a 7 fold change in the expression of the CCL5 gene.

In one example of the method, applying the formulation results in a 3 fold change in the expression of the IGFBP3 gene.

In one example of the method, applying the formulation results in a 2.5 fold change in expression of the SMAD7 gene.

In one example of the method, applying the formulation results in a 2 fold change in expression of the VEGFA gene.

In one example of the method, applying the formulation results in a 1.5 fold decline in expression of the KLK5 gene.

In one example of the method, applying the formulation results in a 1 fold decline in expression of the KLK7 gene.

In one example of the method, applying the formulation results in a 2 fold change in expression of the SOD2 gene.

In one example of the method, applying the formulation stimulates activity of growth factors selected from the group consisting of: INHBA, HGF, GDNF, BTC, EREG, IL11, GDF15, BMP2, BDNF, FGF2, CSF2, CSF3, CXCL1, BMP6, and NRG1.

Thus have been disclosed novel compositions of a *Cordyceps* extract, such as *C. sinensis* and methods of treating dermatological conditions, stimulating gene expression, and stimulating activity of growth factors. Methods for the production of these compositions have also been described. It will be readily apparent to those skilled in the art, that various changes and modifications of an obvious nature may be made without departing from the spirit of the disclosed invention embodiments, and all such changes and modifications are considered to fall within the scope of the invention as recited herein, including in the appended claims. One example of such changes and modifications could include, but is not limited to, adding additional ingredients to the formulations. Other examples of such changes or modifications could include the use of herbs or other botanical products containing the combinations of the preferred embodiments disclosed above.

What is claimed:

1. A topical formulation for treating a dermatological condition comprising,
   from about 0.5% wt % to about 5 wt % of a *Cordyceps* extract including mannitol and adenosine, wherein the *Cordyceps* extract includes the mannitol at from 5 wt % to about 15 wt % and the adenosine at from about 0.5 wt % to about 3.0 wt % based on a weight of the *Cordyceps* extract, and wherein the *Cordyceps* extract is a liquid extract prepared at an extraction temperature ranging from about 50° C. to about 150° C.,
   preservatives, and
   a pharmaceutically acceptable carrier including from about 0.1 wt % to about 5 wt % of a thickener and from about 1 wt % to about 10 wt % of a non-volatile solvent, based on a total weight of the formulation
   wherein the dermatological condition is a dermatological condition selected from the group consisting of fine lines, wrinkles, mottled pigmentation, skin spots, uneven skin tone, tactile roughness/smoothness, firmness in appearance, and crow's feet.

2. The topical formulation of claim 1, wherein the *Cordyceps* extract is derived from *C. sinensis*.

3. The topical formulation of claim 1, wherein the pharmaceutically acceptable carrier further comprises a volatile solvent.

4. The topical formulation of claim 3, further comprising an odorant.

5. The topical formulation of claim 3, wherein the volatile solvent comprises water.

6. The topical formulation of claim 5, wherein the water comprises greater than about 90 wt % of the total formulation.

7. The topical formulation of claim 1, wherein the non-volatile solvent is selected from the group consisting of butylene glycol, propanediol, propylene glycol, isoprene glycol, pentylene glycol, glycerol, sorbitol, poleythylene glycol, polypropylene glycol, other polyols, other sugar alcohols, and combinations thereof.

8. The topical formulation of claim 1, wherein the non-volatile solvent is butylene glycol.

9. The topical formulation of claim 1, wherein the thickener is a member selected from the group consisting of acrylate/C10-C30 alkyl acrylate cross polymer, polyacrylamide, polyacrylate-13, acrylate copolymers, sodium polyacrylate, taurate copolymer derivatives, xanthum gum, carrageenan, guar gum, sclerotium gum, cellulose gum, hydroxypropylcellulose, methylcellulose, hydroxypropyl methylcellulose, cetyl hydroxyethylcellulose, hydrocolloids, and combinations thereof.

10. The topical formulation of claim 1, wherein the thickener is an acrylate/C10-C30 alkyl acrylate cross polymer.

11. The topical formulation of claim 1, wherein the pH of the formulation is from about 5 to 6.

12. The topical formulation of claim 11, wherein the formulation includes a pH adjuster.

13. The topical formulation of claim 12, wherein the pH adjuster is sodium hydroxide.

14. The topical formulation of claim 1, wherein active constituents in the formulation further comprises a member selected from the group consisting of: uridine, uracil, adenine, inosine, and cordycepin.

15. The topical formulation of claim 1, wherein the *Cordyceps* extract is derived from a member selected from the group consisting of: *O. sinensis, C. sinensis, C. militaris, C. ophioglossoides, C. capita, C. pseudomilitaris,* and *C. cardinalis,* and combinations thereof.

* * * * *